United States Patent [19]

Fast

[11] Patent Number: 5,014,688

[45] Date of Patent: May 14, 1991

[54] PATIENT TREATMENT TABLE

[75] Inventor: Duane Fast, Valley City, N. Dak.

[73] Assignee: Tri W-G, Inc., Valley City, N. Dak.

[21] Appl. No.: 578,876

[22] Filed: Sep. 6, 1990

[51] Int. Cl.[5] .......................... A61F 5/00; A61G 7/005; A61G 13/04

[52] U.S. Cl. .......................................... 128/70; 128/73; 128/74; 269/322; 269/323; 5/62

[58] Field of Search ...................... 128/70, 73, 74, 845; 269/322, 323, 325; 5/60, 62; 247/430

[56] References Cited

U.S. PATENT DOCUMENTS

| | | | |
|---|---|---|---|
| D. 147,741 | 10/1947 | Anderson . | |
| D. 249,359 | 9/1978 | Stott et al. . | |
| D. 250,043 | 10/1978 | Shine | 128/70 |
| D. 260,172 | 8/1981 | Kyle . | |
| 1,190,195 | 7/1916 | Schmidt | 128/74 |
| 1,455,922 | 5/1923 | Miller . | |
| 1,470,362 | 10/1923 | Hawley . | |
| 1,626,471 | 4/1927 | Miller . | |
| 1,735,569 | 11/1929 | Gregory . | |
| 2,381,922 | 8/1945 | Norris | 128/73 |
| 2,898,168 | 8/1959 | Thorpe | 269/325 |
| 3,113,770 | 12/1963 | Rutledge . | |
| 3,609,779 | 10/1971 | Oja et al. . | |
| 4,059,255 | 11/1977 | Perold | 5/62 |
| 4,142,520 | 3/1979 | Herbold . | |
| 4,230,100 | 10/1980 | Moon | 128/70 |
| 4,244,358 | 1/1981 | Pyers . | |
| 4,271,830 | 6/1981 | Moon . | |
| 4,387,888 | 6/1983 | Marinakis . | |
| 4,401,110 | 8/1983 | Ekholm . | |
| 4,648,389 | 3/1987 | Kowalski et al. | 269/323 |

*Primary Examiner*—Richard J. Apley
*Assistant Examiner*—Karen Horowitz
*Attorney, Agent, or Firm*—Merchant, Gould, Smith, Edell, Welter & Schmidt

[57] ABSTRACT

A patient treatment table having a bed supported pivotally by a base wherein the bed also has pivotal footboard mechanism. An actuator extends along the same central plane as a base member which provides elevation for the bed. The actuator not only pivots the bed, but also through a push rod pivots the footboard mechanism.

5 Claims, 4 Drawing Sheets

PATIENT TREATMENT TABLE..

FIELD OF THE INVENTION

The present invention is directed to a table of a type useful for chiropractors or physical therapists. The table is pivotable between a substantially upright position for mounting by the patient and a horizontal position suitable for patient treatment. The table has a footboard which swings out of the way.

BACKGROUND OF THE INVENTION

Tables for use by chiropractors and others are known. In fact, through the years, tables have had various designs for tilting between substantially vertical and substantially horizontal positions while at the same time providing a footboard for standing in the vertical position such that it moves out of the way when the table is tilted to the horizontal position. U.S. Pat. No. 1,455,922 is an example of an early such table, while U.S. Pat. No. 4,648,389 is an example of a much more recent such table. Prior art tables, however, have remained relatively complex. The complexity generally has had the result that tables are limited in usefulness, difficult for users to move, subject to reliability problems due to the many parts, and relatively expensive considering the operational characteristics provided.

SUMMARY OF THE INVENTION

The present invention is directed to a table which provides the necessary operating characteristics, but does so with a simple design thereby leading to less expense and greater reliability. The present table includes a bed with a cushion on a frame such that a longitudinal vertical centered plane is identifiable. The table further includes a base for supporting the bed such that the bed is pivotally attached to the base. Footboard mechanism is pivotally attached to the bed frame. Mechanism for pivoting the bed relative to the base provides movement between substantially vertical and substantially horizontal positions and also provides for movement of the footboard mechanism.

The table is shown in the drawings described briefly hereinafter and is described with particularity in the detailed description provided thereafter.

DETAILED DESCRIPTION OF THE PREFERRED EMBODIMENTS

Figure 1:
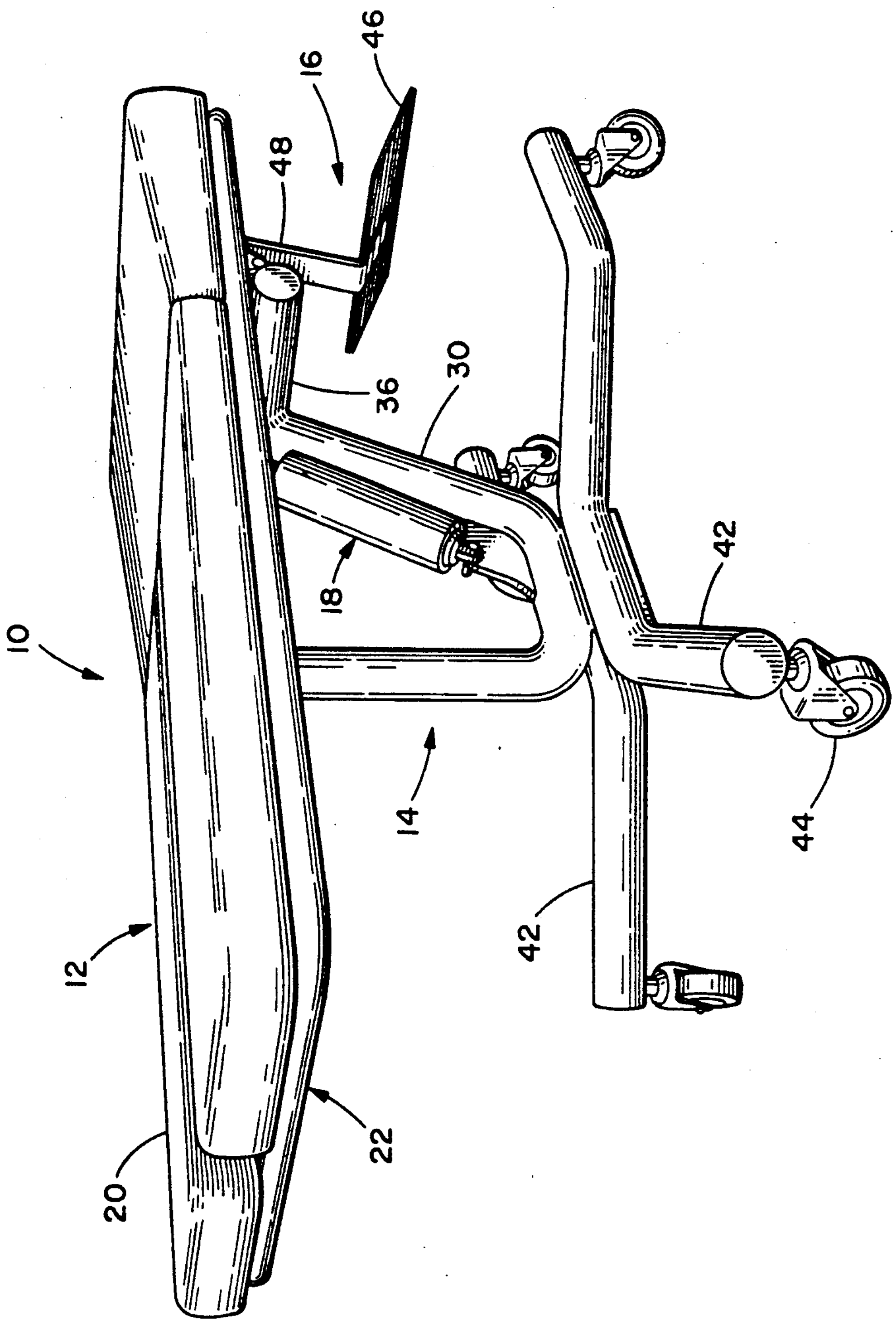
FIG. 1 is a perspective view of a patient treatment table in accordance with the present invention.

Referring now to the drawings wherein like reference numerals designate identical or corresponding parts throughout the several views, and referring more particularly to FIG. 1, a typical patient treatment table in accordance with the present invention is designated generally by the numeral 10. Table 10 includes a bed 12 supported on a base 14. A footboard mechanism 16 is pivotally attached to bed 12 at one end. A drive mechanism 18 pivots bed 12 with respect to base 14 and also pivots footboard mechanism 16 with respect to bed 12.

Figure 4:
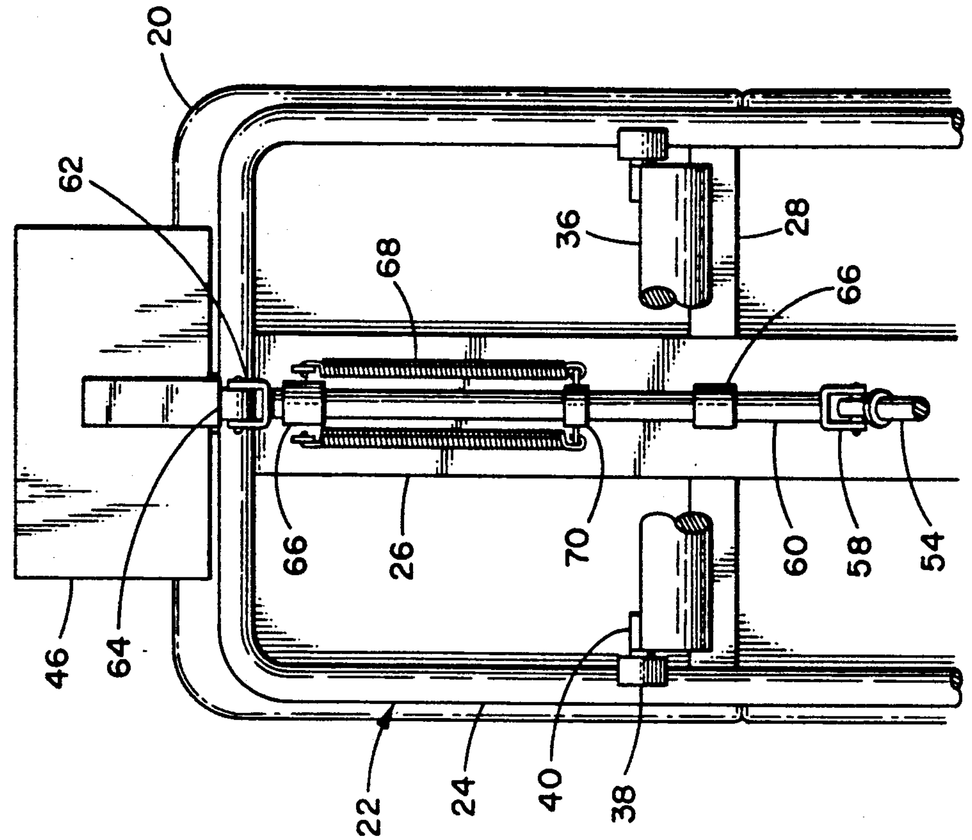
FIG. 4 is a partial bottom view of the bed such that the push rod mechanism is shown.

Bed 12 includes one or more cushions 20 mounted on a frame 22. In the present embodiment, a typical frame 22 is shown more clearly in FIG. 4. Frame 22 includes a rectangular outer member 24 which provides stability at the edges. A central longitudinal member 26 provides rigidity in the lengthwise direction, while at the same time having enough width to provide structure for attaching other mechanisms as described more fully hereinafter. A plurality of transverse members 28 extend between longitudinal member 26 and the longitudinal sides of outer member 24. A longitudinal centerline 25 extends along the center of member 26 and/or is centered between the longitudinal sides of outer member 24. A longitudinal vertical centered plane 27 passes vertically through centerline 25. Although not shown, it may be beneficial to include a rigid sheet member between frame 22 and cushion 20. The various members of the frame are attached together in a conventional way. Likewise, any attachment of the cushion and any sheet member is known.

Figure 2:
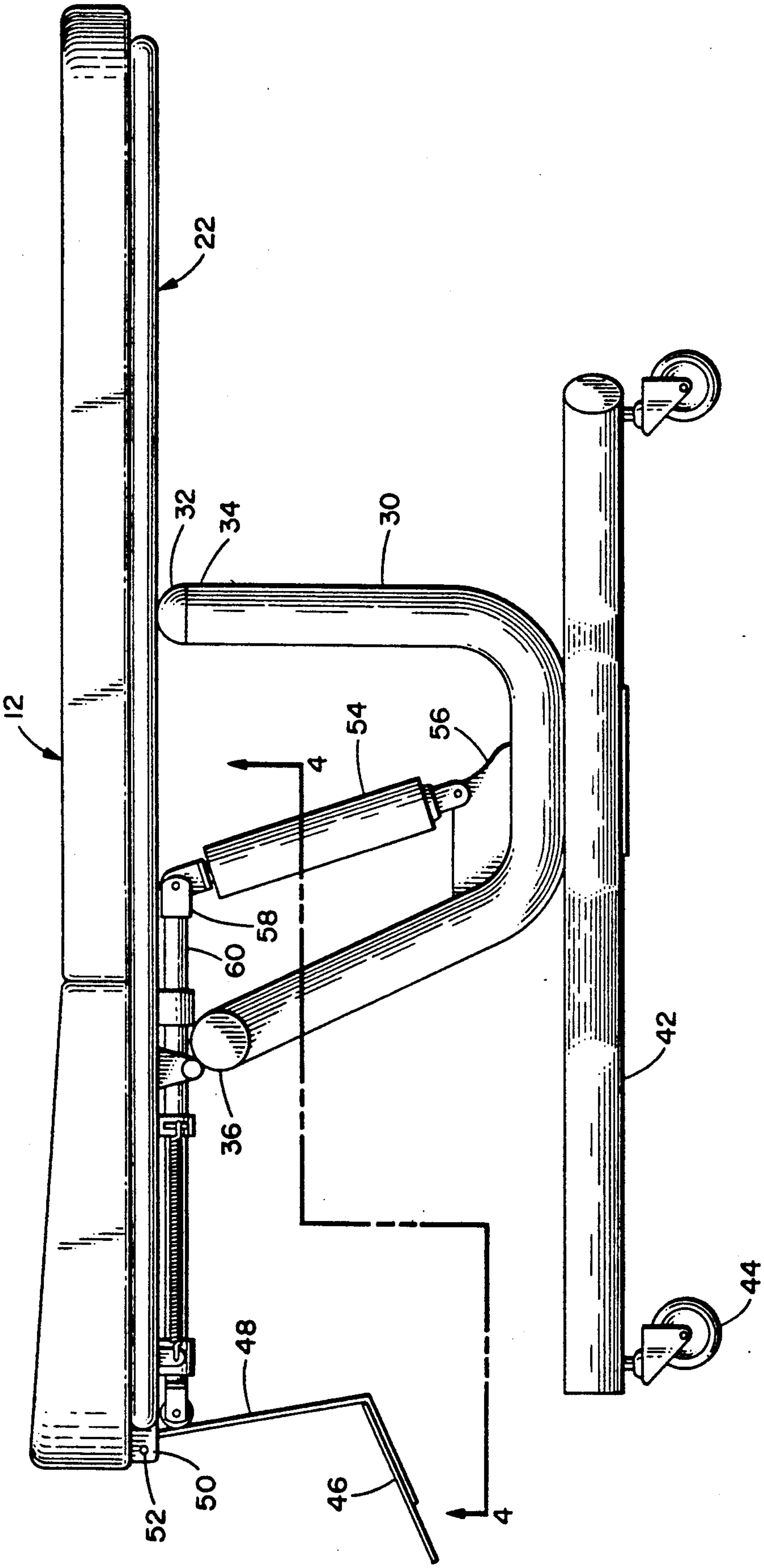
FIG. 2 is a side view of the table of FIG. 1.
Figure 3:
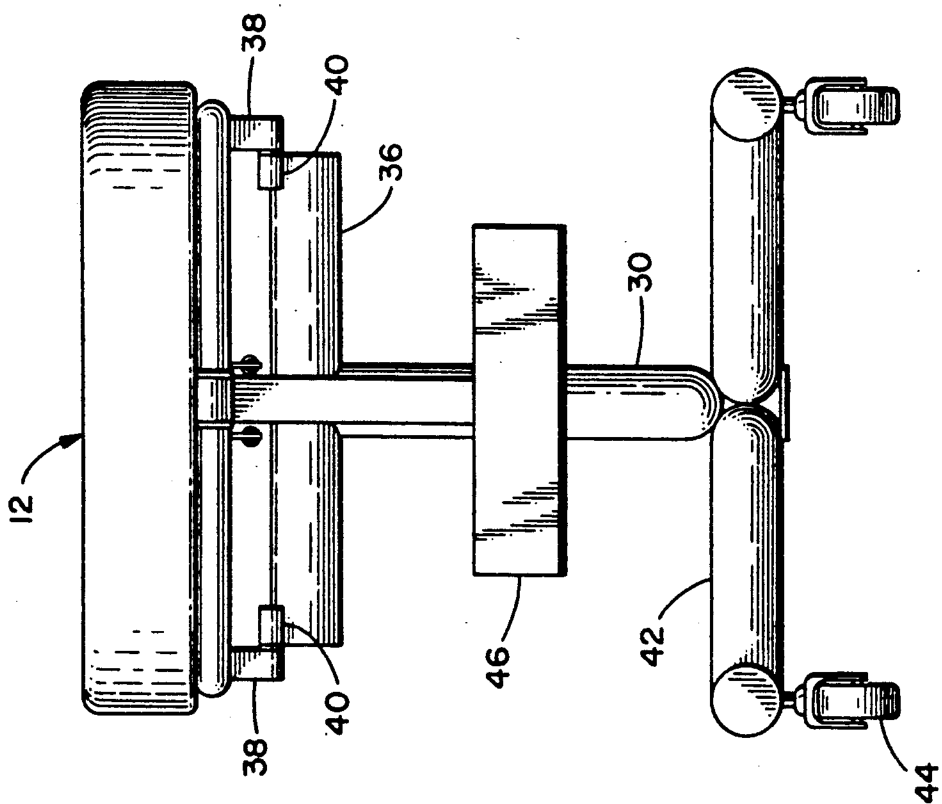
FIG. 3 is a view from the footboard end of the table of FIG. 1.

Base 14 generally comprises a plurality of tubular members welded or otherwise attached together. A first member 30 extends along the centered plane and functions as a support member with respect to supporting the bed 12 in an elevated position with respect to the floor. Member 30, as shown in FIG. 2, has a U-shape with a support element 32 (e.g., a rubber pad) fastened or formed at one end 34. A second member 36 is attached at the other end of first member 30. Second member 36 is tubular and extends transversely to and substantially perpendicular to the centered plane. Frame 22 is pivotally attached to transverse second member 36. As shown in the present embodiment, with reference particularly to FIGS. 3 and 4, a bracket 38 extends downwardly from each longitudinal side of outer member 24. Each bracket may hold a bearing (not shown) or some similar structure for receiving an axle 40 fixedly attached to transverse second member 36. Thus, bed 12 is pivotable about axles 40, and when in the horizontal position, bed 12 is supported not only by axles 40, but also by support element 32 thereby forming a stable three-point supporting structure.

A pair of third members 42 are attached to the bottom or base portion of first member 30 and extend transversely with respect to the centered plane. Each member 42 has a V-shape with a flattened apex fastened to the base portion of member 30. The ends extend transversely outwardly and wheeled casters 44 are attached to each end. Thus, members 42 generally extend along a transverse plane which is spaced from transverse second member 36. Just as with first and second members 30 and 36, members 42 are also preferably tubular.

Footboard mechanism 16 includes a flat sheet 46 which functions as a footboard and an angled flat member 48 which functions as a connecting member between the footboard 46 and frame 22 of bed 12. Footboard 46 is centered on and fixedly attached to one portion of member 48. The other portion of member 48 is pivotally attached to frame 22 as shown in FIG. 2. Bracket members 50 extend outwardly from an end of outer member 24. A pin 52 extends between bracket members 50 and through a cylindrical end portion (not shown) of flat member 48 to provide an appropriate pivotal connection.

Drive mechanism 18 includes an actuator 54 extending between a bracket member 56 welded or otherwise attached to the base portion of U-shaped first member 30 and a clevis 58 at the end of push rod 60. Actuator 54 may be powered electrically or by some other power mechanism and extends along the centered plane. Actuator 54 is inclined rearwardly from bottom to top when bed 12 is horizontal. Such orientation is preferable to prevent during operation any possibility of the actuator and push rod from forming a right angle and either locking in such position or passing through center and extending in a wrong direction.

Figure 5:
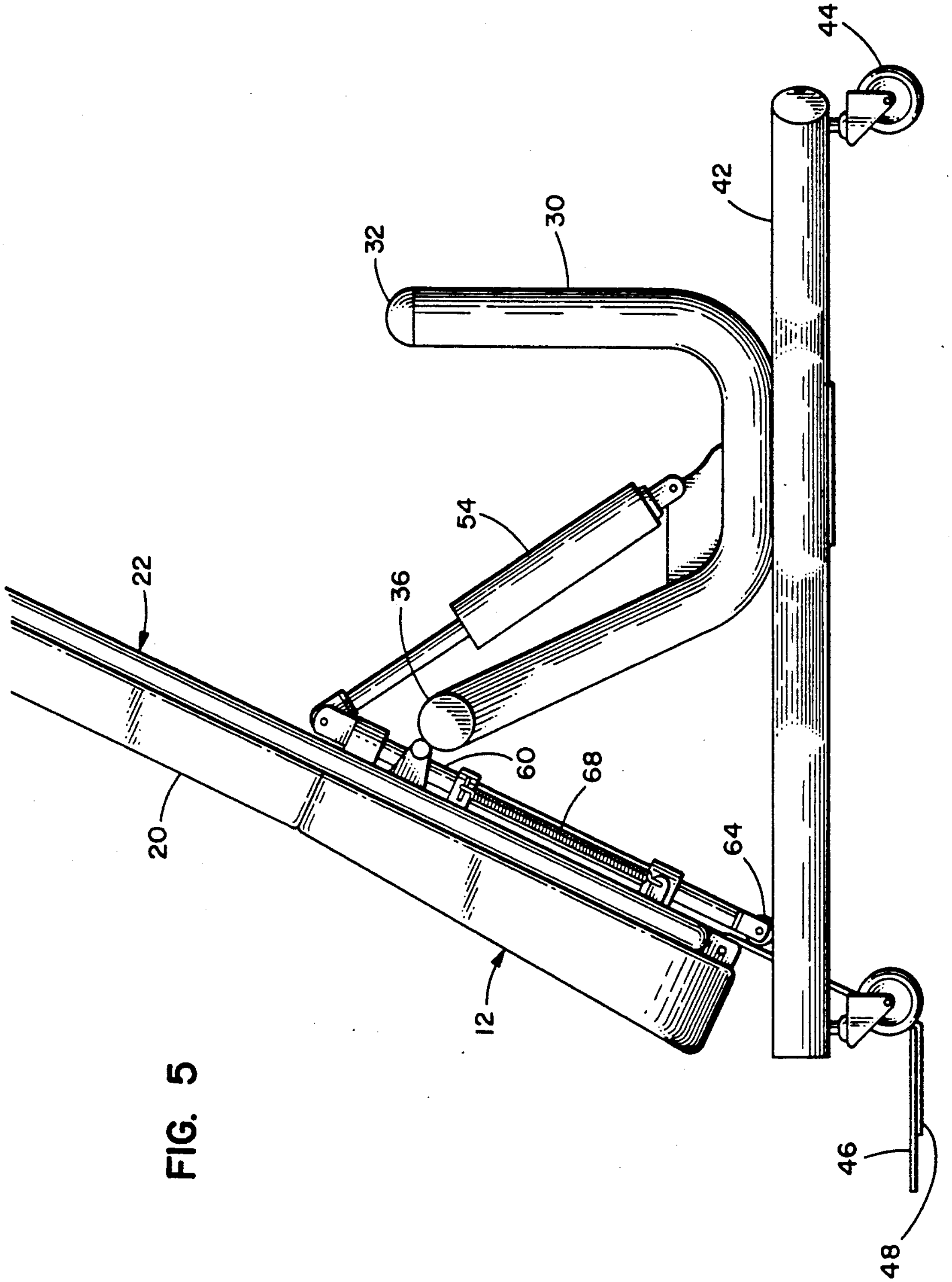
FIG. 5 is a partial side view showing the table in a substantially upright position.

Push rod 60 is a unitary member extending from clevis 58 at the end attached to actuator 54 to a clevis 62 at the other end which holds a roller 64. Roller 64 is aligned with flat member 48 so that when actuator 54 extends and pushes push rod 60, roller 64 moves into contact with flat member 48 and rolls along it to pivot flat member 48 and footboard 46 from a downwardly hanging, out of the way position to a position wherein a patient can contact that bottom of his/her feet when it is in the position as shown in FIG. 5. Push rod 60 is retained relative to longitudinal member 26 of bed frame 22 by a pair of bushings 66. Push rod 60 is forcefully biased in the direction of footboard mechanism 16 by a pair of coil springs 68 in tension. Springs 68 extend from a bracket 70 fixedly attached to push rod 60 and the rearwardmost bushing 66.

In use, actuator 54 is extended so that it pushes angularly against push rod 60 which is retained with bushings 66 to frame 22. In this way, as actuator 54 extends, it pivots bed 12 about axles 40. At the same time, push rod 60 slides through bushings 66 under the aid of springs 68. Roller 64 comes into contact with flat member 48 and pivots the footboard mechanism 16 so that footboard 46 approaches a right angle position with bed 12. As shown in FIG. 5, in this way a patient can stand on footboard 46 and lean against cushion 20. One of the patient is mounted, the action just described is reversed. That is, the actuator 54 is operated in reverse to contract and pull push rod 60 forwardly. In doing so, bed 12 pivots downwardly into the horizontal position and push rod 60 retracts so that footboard mechanism 16 swings downwardly and out of the way. Actuator 54 contracts until frame 22 makes contact with support element 32.

The present patient treatment table 10 is particular advantageous in that the base mechanism has a simple, yet structurally stable design. A single member provides for vertical elevation. It does so along a central plane in order to provide maximum support. Three point contact is maintained due to support element 32 being spaced from brackets 38 and axles 40.

The footboard mechanism of the present invention provides the necessary operational characteristics, but does so with a minimum of parts. A single push rod is used between the actuator and the member connecting the footboard and the frame of the bed. Because of the location of the connection between the push rod and the actuator and because the push rod is retained to the frame of the bed, the single actuator also controls the pivoting of the bed with respect to the base.

The present structural configuration is able to maintain a minimum of parts since so many of the parts are aligned on the central plane where the structure is the strongest and is consequently also transversely symmetrical. The first base member 30 is on the central plane, as is actuator 54 and push rod 60. Furthermore, flat plate 48 also extends along the central plane to allow contact with roller 64.

Finally, although the present patient treatment table has thus been described with particularity and its advantages discussed, it is understood that the disclosure is representative and that equivalents are possible. For example, hinges of various types may be used at the pivots. The various frame and base members may be made from structural elements other than round or square tubes. The actuator may have any type of power source. The springs could be of another type. Since this is only an exemplary listing of equivalents, it must therefore be understood that changes made in the preferred embodiment, especially in matters of shape, size, and arrangement are also within the principle of the present invention to the full extent extended by the general meaning of the terms in which the appended claims define the invention.

What is claimed is:

1. A patient treatment table, comprising:

a bed including a cushion on a frame, said frame having a longitudinal vertical centered plane;

base means for supporting said bed;

first means for pivotally connecting said bed frame to said base means;

footboard means including a footboard and second means for pivotally connecting said footboard to said frame;

a push rod extending along said centered plane, said push rod having a free end to slidingly cam said footboard means;

means for retaining said push rod relative to said bed frame; and means, attached to said push rod, for driving said push rod and causing pivoting at both said first and second connecting means.

2. The patient treatment table in accordance with claim 1 including means for biasing said push rod toward said footboard.

3. A patient treatment table, comprising:

a bed including a cushion on a frame, said frame having a longitudinal vertical centered plane;

base means for supporting said bed, said base means including a first member extending along said centered plane, said base means further including a second member transverse to and substantially perpendicular to said centered plane, said second member being attached fixedly at a first location to said first member and being attached pivotally to said bed frame, said base means also including a support element for said bed, said support element being attached at a second location to said first member, said first and second locations being spaced apart;

a footboard pivotally attached to said bed frame; and means for sumultaneously pivoting both said bed relative to said base means and said footboard relative to said bed frame.

4. The patient treatment table in accordance with claim 3 wherein said base means also includes a third member attached to said first member, said third member being in a transverse plane spaced from said second member.

5. A patient treatment table, comprising:

a bed including a cushion on a frame, said frame having a longitudinal vertical centered plane;

base means for supporting said bed, said base means having a support member which function with respect to said bed for supporting said bed in an elevated position;

first means for pivotally connecting said bed frame to said base means;

footboard means including a footboard and second means for pivotally connecting said footboard to said frame;

a push rod; and means for driving said push rod and causing pivoting at both said first and second connecting means, said support member, said push rod and said driving means all extending along said centered plane.

* * * * *